(12) United States Patent
Morales

(10) Patent No.: US 7,219,884 B2
(45) Date of Patent: May 22, 2007

(54) PATHOLOGY GROSSING TOOL

(75) Inventor: Azorides R. Morales, Miami, FL (US)

(73) Assignee: The University of Miami, Miami, FL (US)

( * ) Notice: Subject to any disclaimer, the term of this patent is extended or adjusted under 35 U.S.C. 154(b) by 564 days.

(21) Appl. No.: 10/260,443

(22) Filed: Oct. 1, 2002

(65) Prior Publication Data

US 2004/0061269 A1   Apr. 1, 2004

(51) Int. Cl.
*B23Q 1/00* (2006.01)
(52) U.S. Cl. ........................................ 269/53
(58) Field of Classification Search ............ 254/131.5, 254/132; 269/53, 54–54.5; 30/322, 323, 30/147–150, 137; 132/126, 219, 139, 142, 132/152; D7/653; 294/120, 55.5, 49
See application file for complete search history.

(56) References Cited

U.S. PATENT DOCUMENTS

| | | | |
|---|---|---|---|
| 1,390,870 A | 9/1921 | Bittle | |
| 1,893,258 A * | 1/1933 | Washburn | 172/21 |
| D109,133 S | 4/1938 | Galleazzi | |
| D168,127 S | 11/1952 | Schoenfeld | |
| 3,061,270 A * | 10/1962 | Lowe | 254/132 |
| 3,838,474 A * | 10/1974 | Erickson | 15/142 |
| 4,930,824 A * | 6/1990 | Matthews et al. | 294/19.1 |
| 5,318,051 A * | 6/1994 | Koppel | 132/126 |
| 5,611,266 A | 3/1997 | Kensrue | |
| 5,884,633 A * | 3/1999 | Ford | 132/137 |
| 6,207,408 B1 | 3/2001 | Essenfeld et al. | |
| 6,290,211 B1 * | 9/2001 | Pheiffer | 254/132 |
| 2002/0020276 A1 | 2/2002 | Morales et al. | |

* cited by examiner

*Primary Examiner*—Robert C. Watson
(74) *Attorney, Agent, or Firm*—Nixon & Vanderhye PC

(57) ABSTRACT

A tool for holding tissue to be sampled in place to allow tissue samples of a prescribed thickness to be prepared from the held tissue. The tool includes at least one tine array for engaging and holding the tissue. First and second tine arrays may advantageously be provided to define a slice thickness therebetween. In addition, or in the alternative, the tines of the tine array are mutually spaced apart by different distances to effectively hold the tissue and to define prescribed tissue sample lengths.

11 Claims, 6 Drawing Sheets

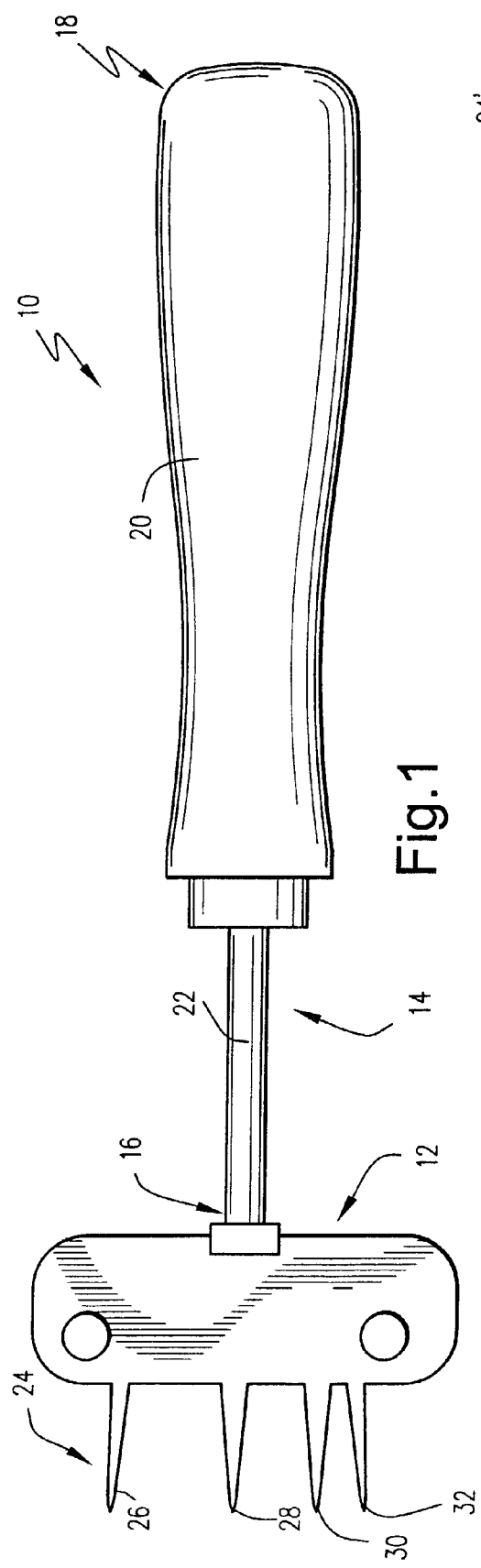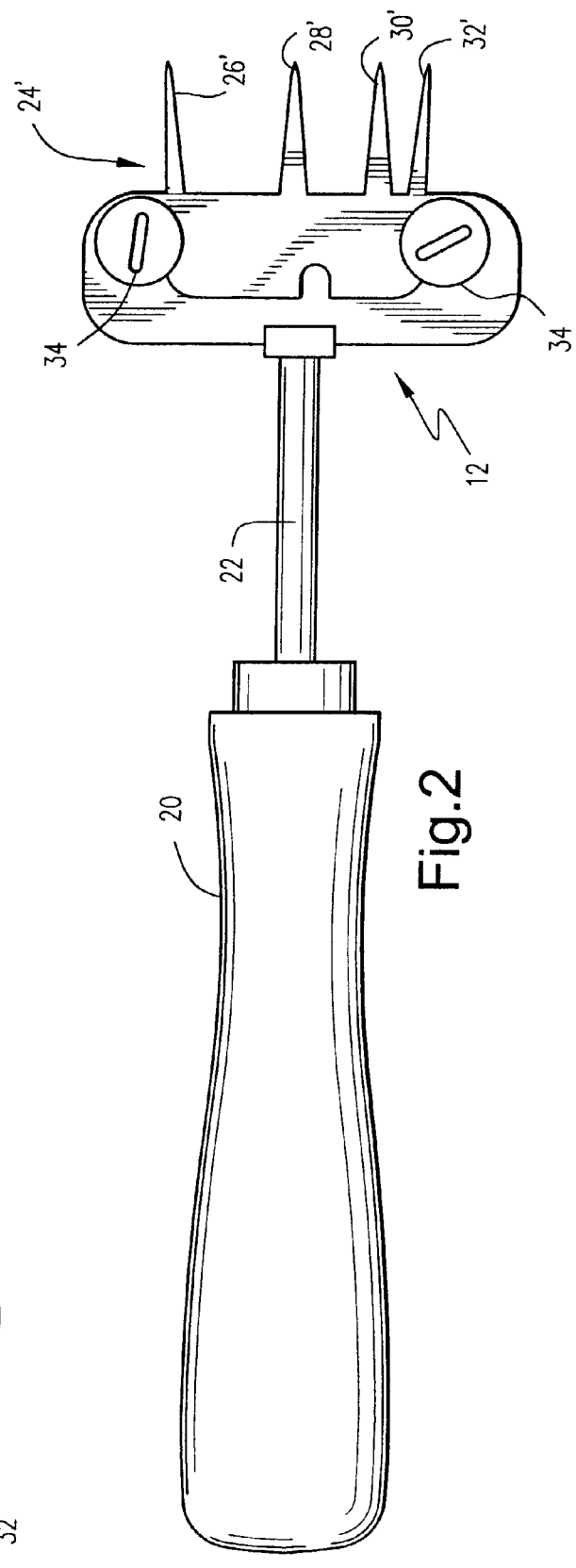

PATHOLOGY GROSSING TOOL

BACKGROUND OF THE INVENTION

The invention relates to devices and tools used to prepare tissue samples and, more particularly, to a grossing tool for preparing slices of tissue uniformly of a desired thickness.

In the field of pathology, it is customary to prepare slice-shaped tissue samples for processing, mictrotomy, staining and histopathologic analysis. The term 'grossing' refers to the handling and preparation of a relatively thick tissue sample, i.e., samples on the order of 0.5 to 4 millimeters in thickness. Grossing is in contrast to microtomy, in which extremely thin tissue samples, i.e., samples on the order of 3 to 10 microns in thickness, are prepared.

When preparing relatively thick slices from various tissue samples, i.e., when grossing multiple specimens, it is important for the slices of tissue to be as consistently uniform in thickness as possible to facilitate standardization of the tissue processing method. A grossing board has been developed which facilitates the preparation of gross tissue samples that are of a desired thickness. The grossing board, which is the subject of U.S. application Ser. No. 09/876,167, the entire disclosure of which is incorporated herein by this reference, has one or more tissue-receiving depressions formed therein. A knife-guiding assembly is provided to guide a knife or scalpel blade along the surface of the grossing board to cut the tissue sample to a desired thickness as defined by the depth of the respective depression.

While the grossing board greatly facilitates the preparation of tissue samples for processing, it remains difficult to sample flat structures such as skin, intestine and the like as well as small tubular organs such as the appendix and fallopian tubes. Also, organs such as the bowel and gallbladder, which are composed of layers of different structures that slide over each other during sectioning present problems to pathologists. Indeed, these tissues are particularly difficult to slice during grossing and practically impossible to section uniformly at the desired thickness.

Additionally, tissues that are very soft, smooth and slippery, such as those having a high fat content, are difficult to hold on any cutting surface to section appropriately. This is the case with, for example, breast, skin with subcutaneous fat, and tumors of adipose tissue. It is the present practice to hold such tissues with forceps while slicing them to prepare samples for processing. However, the sections obtained in this manner are irregular, varying considerably in dimension and thickness.

Therefore, there remains a need for a device to facilitate the preparation of tissue samples of the desired thickness, particularly where the above-described grossing board cannot easily be utilized.

SUMMARY OF THE INVENTION

The present invention provides a tool that effectively holds the tissue to be sampled in place to allow tissue samples of a prescribed thickness to be prepared from the held tissue. The tool greatly facilitates handling the above-mentioned organs and others during grossing and leads to the standardization of tissue samples for processing.

More specifically, the invention may be embodied in a pathology grossing tool comprising: a tine supporting head; a main body having a longitudinal axis and distal and proximal ends, said main body including a handle portion terminating at said proximal end thereof, said main body being coupled to said tine supporting head at said distal end thereof; and at least one array of tines projecting from said tine supporting head, each array of tines being defined in a plane and comprising at least three tines, each said tine terminating in a sharp tissue penetrating tip, a first mutually adjacent pair of said tines of said array being laterally spaced apart by a distance that differs from a lateral spacing of a second mutually adjacent pair of tines of said array. The varying tine spacing allows an appropriate tine pair to be used to hold the tissue during slicing, depending upon the tissue type and size, and can be used to determine the length of the sample prepared from the specimen.

The invention may also be embodied in a pathology grossing tool comprising: a tine supporting head; a plurality of tines projecting from said tine supporting head, each said tine terminating in a sharp tissue penetrating tip; a main body having a longitudinal axis and distal and proximal ends, said main body including a handle portion terminating at said proximal end thereof, said main body being coupled to said tine supporting head at said distal end thereof; and wherein there are first and second arrays of tines projecting from said tine supporting head, said arrays of tines each being defined in a plane, said tine arrays being disposed in parallel so as to define a gap therebetween, each tine of said first tine array being disposed in adjacent parallel, facing relation to a corresponding tine of said second tine array. The parallel tine arrays facilitate the preparation of a uniformly thick tissue sample.

The tines of the parallel tine arrays may be uniformly distributed transversely of the tine supporting head or, in the alternative may define varying tine spaces, thereby to facilitate the preparation of tissue samples of prescribed length.

BRIEF DESCRIPTION OF THE DRAWINGS

These and other objects and advantages of this invention, will be more completely understood and appreciated by careful study of the following more detailed description of the presently preferred exemplary embodiments of the invention taken in conjunction with the accompanying drawings, in which:

FIG. 1 is a plan view of a first face of a tissue grossing tool according to a first embodiment of the invention;

FIG. 2 is a plan view of a second face of the tool of FIG. 1;

DETAILED DESCRIPTION OF THE INVENTION

Figure 3:
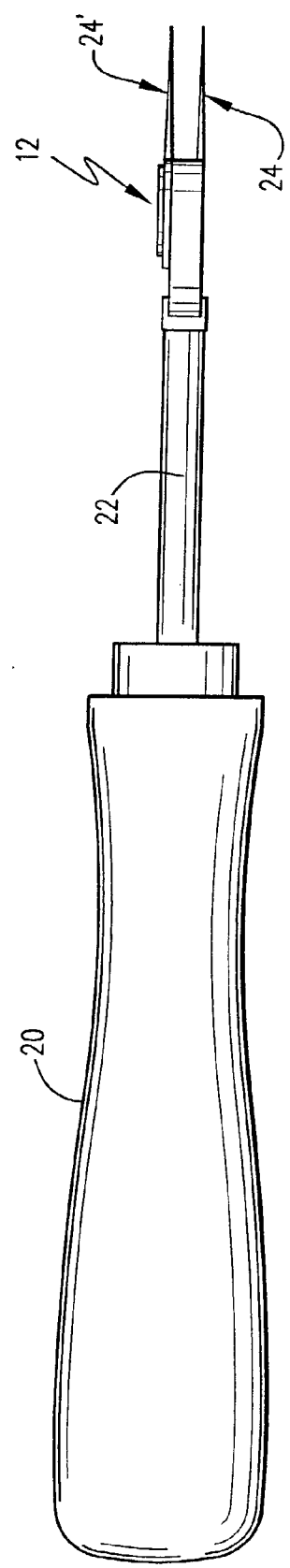
FIG. 3 is a side elevational view of the tool of FIGS. 1 and 2.

In an first exemplary embodiment, the pathology grossing tool 10 of the invention comprises a tine supporting head 12 and a main body 14 having a longitudinal axis and distal and proximal ends 16,18. The tool body 14 includes a handle portion 20 terminating at the proximal end 18 and a shaft 22 connecting tine supporting head 12 to handle 20. A plurality of prongs or tines project from the tine-supporting head.

Each array 24 of tines is comprised of at least three tines with the illustrated embodiment depicting four tines 26,28, 30,32.

In the embodiment illustrated in FIGS. 1–4, a first mutually adjacent pair of tines, e.g., 26,28 are laterally spaced apart by a distance that differs from a lateral spacing of another mutually adjacent pair of tines, e.g., 28,30. In this example, the mutually adjacent pairs of tines are spaced at 1.5, 1.0, and 0.5 centimeters apart. The variety of the spacings allows an appropriate tine pair or set to be used depending upon the tissue type and size and can be used to determine the length of the sample prepared from the specimen as described hereinbelow.

In the illustrated and presently preferred embodiments, first and second parallel tine arrays are provided to ensure secure anchoring of the tissue for sample preparation and to define the thickness of the tissue sample. The facing prongs or tines of the adjacent arrays are spaced apart to define a gap of about 1 to 2 millimeters, and more preferably about 1.5 millimeters to obtain sections of that particular thickness.

In the embodiment illustrated in FIGS. 1–4, one of the tine arrays 24 integrally projects from the tine supporting head 12 whereas the other tine array 24' is separately formed and secured, e.g., with fasteners, such as bolts 34 or the like, to the supporting head 12. As such, the thickness of the head defines the gap between the tine arrays and thus the thickness of the tissue slice defined by the tine arrays 24, 24'. It is to be understood, however, that both tine arrays may be detachably secured to the tine supporting head. In this manner, the tine arrays may be removed for cleaning or interchanged, e.g., with other tine arrays providing a different tine spacing or tine shape, and/or a different tine gap, as may be appropriate for different tissue or organ types.

Figure 5:
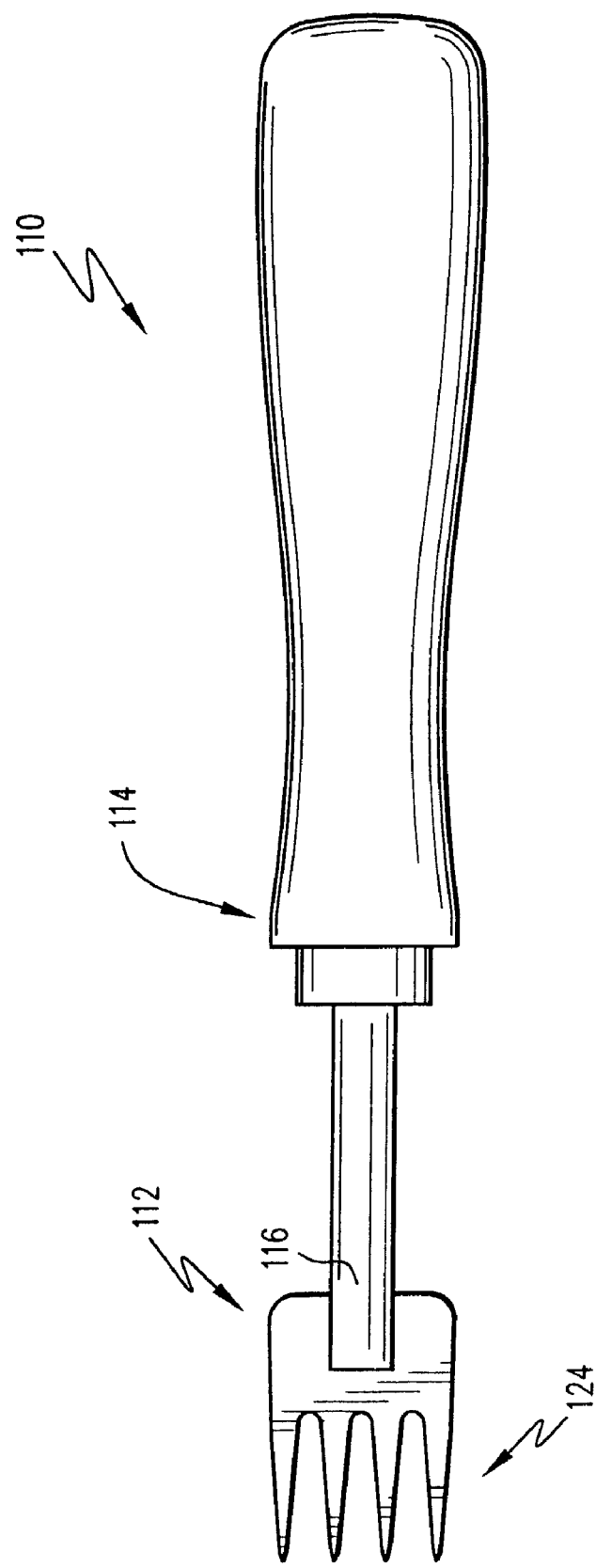
FIG. 5 is a plan view of a first face of a tissue grossing tool according to a second embodiment of the invention.
Figure 6:
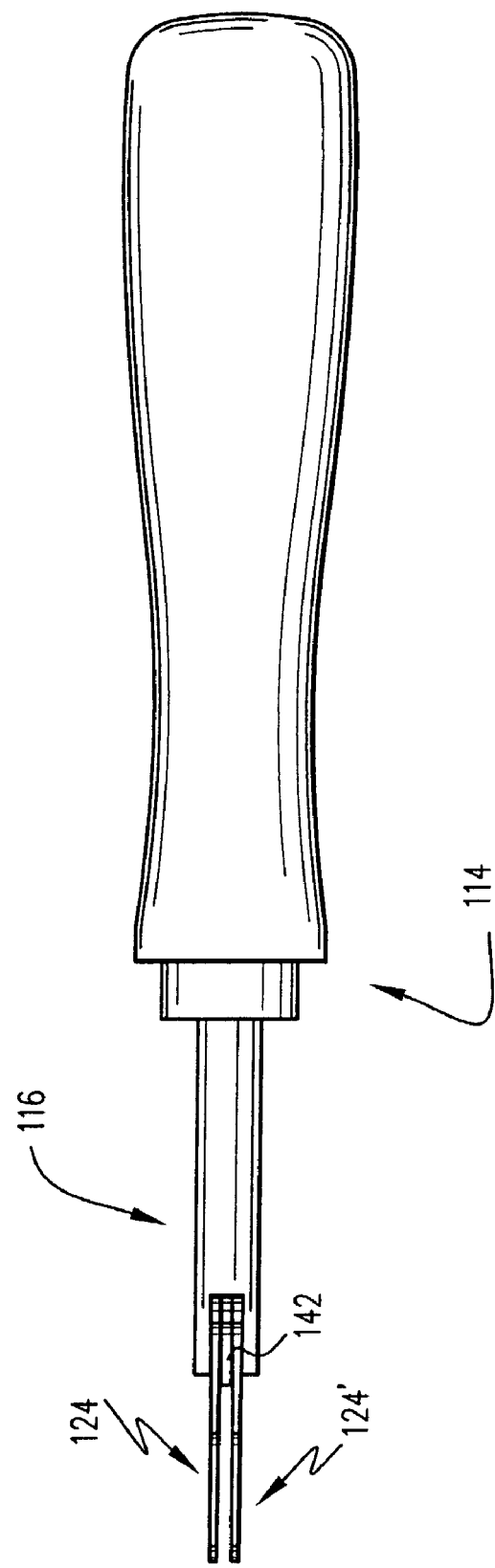
FIG. 6 is a side elevational view of the tool of FIG. 5.
Figure 7:
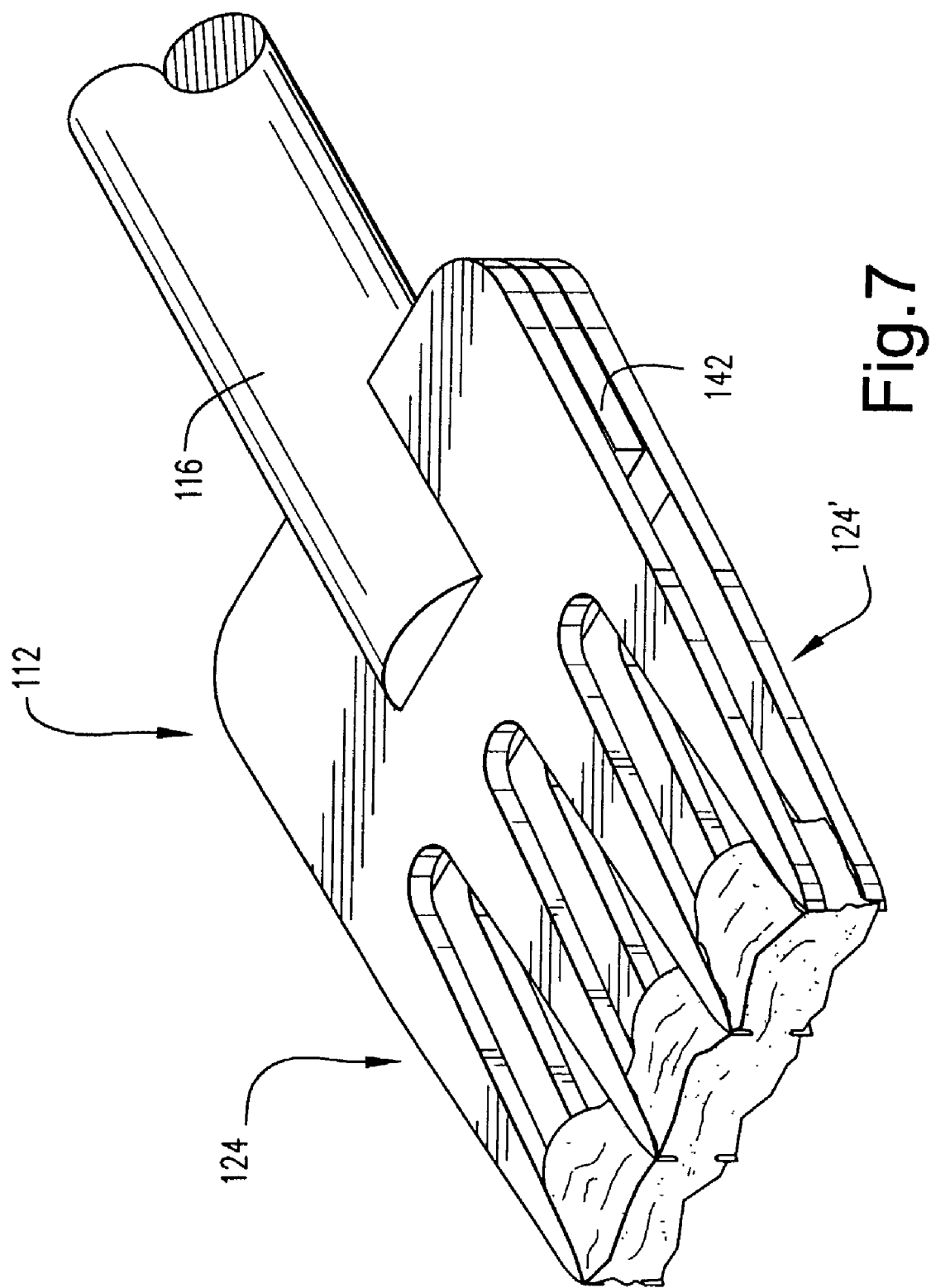
FIG. 7 is a schematic illustration showing a slice of tissue disposed between the parallel tine arrays of the tool of FIG. 5, after cutting along front and rear faces, and end edges of the tool.

FIGS. 5–7 depict a second, presently preferred embodiment of the invention. For ease of explanation, the tool components are labeled with reference numbers corresponding to those used for the corresponding components in the first embodiment, but incremented by 100. A description of the components is omitted except as necessary or desirable to differentiate this embodiment from the first embodiment.

In the embodiment illustrated in FIGS. 5–7, the tine supporting head 112 of the tool 110 is comprised of a base of each of the tine arrays 124, 124' and a spacer structure 142 disposed therebetween. The tine arrays and spacer are attached to one another and to the slotted distal end 116 of the shaft 222 of the tool main body 114 by, for example, welding. As such, the thickness of the spacer defines the gap between the tine arrays and the distance between the tine array outer faces defines the thickness of the tissue slice that can be prepared with the tool, as shown in FIG. 7. An advantage of this embodiment is that the tool need not include lateral shoulders to accommodate fasteners, thus minimizing visual obstruction of the tissue specimen and the tissue slicing process.

The embodiment of FIGS. 5–7 also differs from the first embodiment in that the tines are uniformly distributed in each tine array. The tines may be spaced apart by about 0.5 cm to define tissue sample lengths of about 0.5, 1.0 and 1.5 centimeters. Other tine spacings may be provided as deemed necessary or desirable for securing the tissue during slicing and/or to define preferred sample lengths.

To hold the tissue in position during cutting, the prongs or tines of the device each terminate in a sharp, pointed tip, to facilitate penetration of the tissue with minimal disruption. As is apparent, securing specimens, particularly specimens of tissues, such as the intestines and gallbladder, with the tines prevents the various layers of tissue from sliding upon each other during the cutting process. By holding the tissue to a cutting board with the prongs or tines of the instrument, suitable slices of tissue can be obtained by cutting parallel to or between the prongs, as described more particularly below. In the illustrated embodiment, the tines have a length on the order of 1 to 3 centimeters, but may have a greater length as necessary or desirable to accommodate a variety of specimens. The handle is about 8 to 10 centimeters in length and is separated from the tine supporting head by, e.g., 2 to 4 centimeters to facilitate manipulation of the instrument, visualization of the specimen, and proper gripping during tissue slicing.

Figure 4:
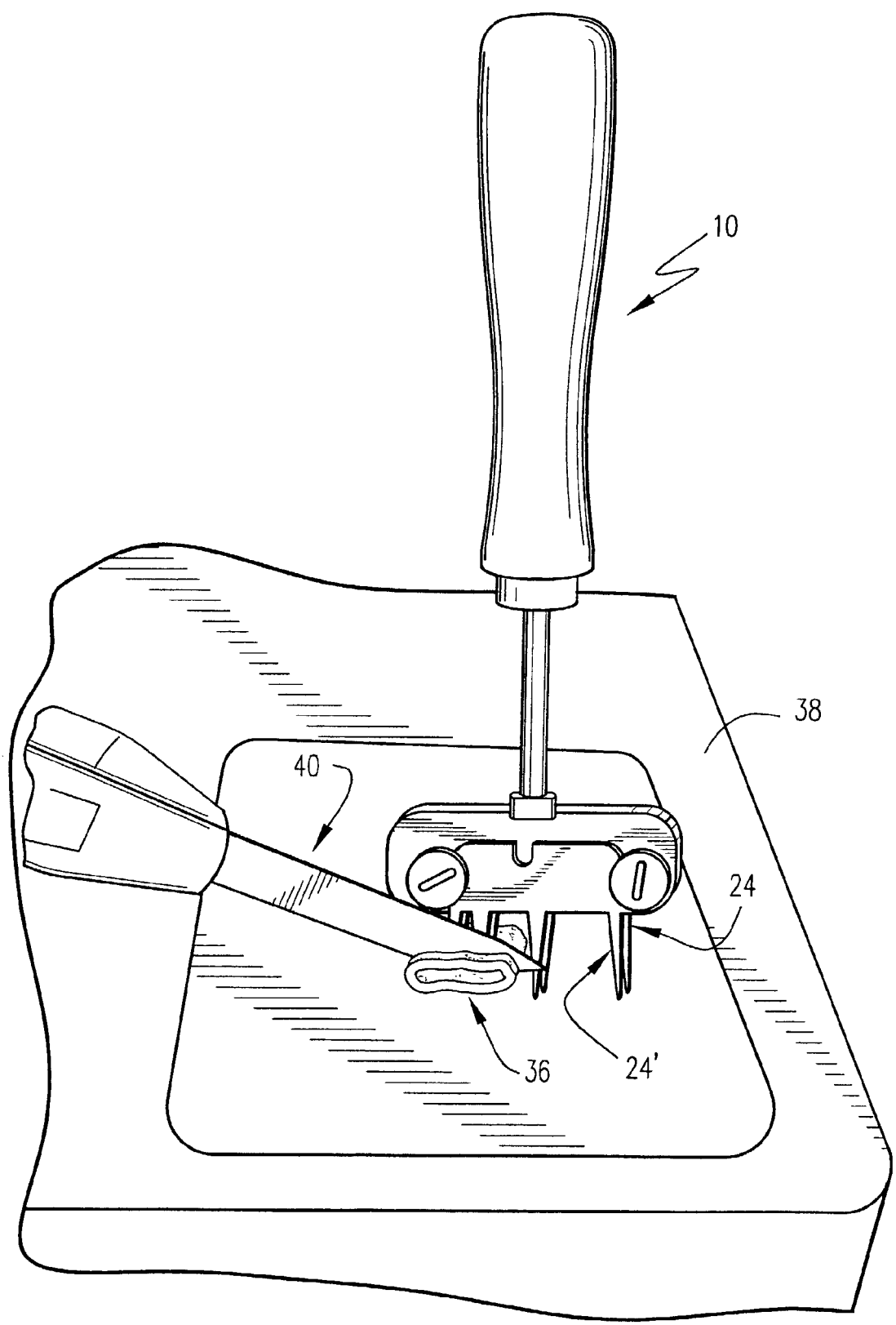
FIG. 4 is a schematic illustration showing the cutting of a tissue held with the grossing tool of FIG. 1.

As schematically illustrated in FIG. 4, during grossing, the tissue 36 is held on e.g., a cutting board 38 with the tool 10 as mentioned above. To obtain samples, a knife or scalpel 38 is used to slice along the outer surfaces of each array 24, 24' of tines. Thus, as illustrated in FIG. 7, the sample to be processed remains between the double set or parallel arrays of tines. The length of the slice or strip of tissue so obtained is established as desired by slicing transverse to the tine arrays, guided by the side edges of the respective tines and/or as determined by the length dimension of the tissue specimen in a direction transverse to the long axis of the tool and parallel to the arrays.

The tines array(s) 24, 24'; 124, 124' or more specifically, the plane including each array of tines is disposed in the illustrated embodiment so as to include or so as to be parallel to the longitudinal axis of the main body 14, 114 of the tool so that the tines project longitudinally from the distal end of the tine supporting head 12, 112. It is to be understood, however, that the plane of the tine array(s) may be inclined at an angle with respect to the longitudinal axis of the main body to increase user comfort and/or facilitate visualization of the tissue sample.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A pathology grossing tool comprising:
   a tine supporting head;
   a plurality of tines projecting from said tine supporting head, each said tine terminating in a sharp tissue penetrating tip;
   a main body having a longitudinal axis and distal and proximal ends, said main body including a handle portion terminating at said proximal end thereof, said main body being coupled to said tine supporting head at said distal end thereof; and wherein there are first and second arrays of tines projecting distally from said tine supporting head, said arrays of tines each being defined in a plane, said tine arrays being disposed in parallel so as to define a gap therebetween, each tine of said first tine array being disposed in adjacent parallel, facing relation to a corresponding tine of said second tine array, wherein said gap defined between said tine arrays is about 1 to 2 millimeters.

2. A pathology grossing tool as in claim 1, wherein a first mutually adjacent pair of said tines of said first tine array are laterally spaced apart by a distance that differs from a lateral spacing of a second mutually adjacent pair of tines of said first tine array.

3. A pathology grossing tool as in claim 1, wherein said tines are uniformly distributed in each said array.

4. A pathology grossing tool as in claim 1, wherein at least one of said tine arrays is formed separately from said tine support head and secured thereto.

5. A pathology grossing tool as in claim 4, wherein said at least one tine array is secured to said tine supporting head with fasteners.

6. A pathology grossing tool as in claim 1, wherein said tine arrays are welded to define said tine supporting head.

7. A pathology grossing tool as in claim 1, wherein each said tine array comprises a tine base supporting a plurality of tine elements and wherein said tine supporting head is comprised of said tine bases and a spacer component disposed therebetween to define said gap.

8. A pathology grossing tool as in claim 1, wherein said gap defined between said tine arrays is about 1.5 millimeters.

9. A pathology grossing tool as in claim 1, wherein each said tine array comprises four tines.

10. A pathology grossing tool as in claim 1, wherein said planes of said tine arrays are parallel to said longitudinal axis of said main body.

11. A pathology grossing tool comprising:
a tine supporting head;
a plurality of tines projecting from said tine supporting head, each said tine terminating in a sharp tissue penetrating tip; and
a main body having a longitudinal axis and distal and proximal ends, said main body including a handle portion terminating at said proximal end thereof, said main body being coupled to said tine supporting head at said distal end thereof;
wherein there are first and second arrays of tines projecting distally from said tine supporting head, said arrays of tines each being defined in a plane, said tine arrays being disposed in parallel so as to define a gap therebetween, each tine of said first tine array being disposed in adjacent parallel, facing relation to a corresponding tine of said second tine array, and
wherein each said tine array comprises a tine base supporting a plurality of tine elements and wherein said tine supporting head is comprised of said tine bases and a spacer component disposed therebetween to define said gap between said tine arrays.

* * * * *